United States Patent [19]
Blondel et al.

[11] 3,959,268
[45] *May 25, 1976

[54] PHENTHIAZINE DERIVATIVES

[75] Inventors: Jean-Claude René Georges Blondel, Savigny-sur-Orge (Essonne); Jean Clément Louis Fouché, Bourg-la-Reine (Hauts-de-Seine); Claude Georges Alexandre Guérem' y, Creteil (Val-de-Marne), all of France

[73] Assignee: Rhone-Poulenc, S.A., Paris, France

[ * ] Notice: The portion of the term of this patent subsequent to Apr. 1, 1992, has been disclaimed.

[22] Filed: Nov. 14, 1974

[21] Appl. No.: 523,750

[30] Foreign Application Priority Data

Mar. 29, 1967 France .......................... 67.1000663

[52] U.S. Cl. ............................ 260/243 A; 424/247
[51] Int. Cl.² ........................................ C07D 279/28
[58] Field of Search ................. 260/243 A; 424/247

[56] References Cited
UNITED STATES PATENTS

| | | | |
|---|---|---|---|
| 3,075,976 | 1/1963 | Jacob et al. ...................... | 260/243 A |
| 3,194,733 | 7/1975 | Yale et al. ...................... | 260/243 A |
| 3,350,268 | 10/1967 | Yale et al. ...................... | 260/243 A |
| 3,875,156 | 4/1975 | Blondel et al. .................. | 260/243 A |
| 3,879,551 | 4/1975 | Blondel et al. .................. | 424/247 |

FOREIGN PATENTS OR APPLICATIONS 904,208   8/1962   United Kingdom ............ 260/243 A Primary Examiner—John D. Randolph
Attorney, Agent, or Firm—Stevens, Davis, Miller & Mosher

[57] ABSTRACT

Phenthiazine derivatives of the formula:

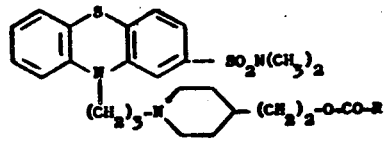

wherein R represents an alkyl, alkenyl or alkynyl group containing 7–17 carbon atoms, are very active as long acting neuroleptics anti-emetics and tranquilisers.

2 Claims, No Drawings

PHENTHIAZINE DERIVATIVES

This application is a divisional application of Ser. No. 181,619 filed Sept. 17, 1971, now U.S. Pat. No. 3,879,551 granted Apr. 22, 1975, which was a continuation of Ser. No. 49,192 filed June 23, 1970, and now abandoned, which in turn was a continuation-in-part of Ser. No. 717,012 filed Mar. 28th, 1968, now U.S. Pat. No. 3,875,156 granted Apr. 1, 1975.

This invention relates to new therapeutically useful phenthiazine derivatives, to processes for their preparation and pharmaceutical compositions containing them.

According to the present invention, there are provided the new phenthiazine derivatives of the general formula:

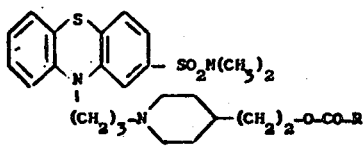

I wherein R represents a straight or branched alkyl, alkenyl or alkynyl group containing 7–17 carbon atoms, for example 1-ethylpentyl, 1-methylhexyl, heptyl, 1,1-dimethylhexyl, octyl, nonyl, non-1-enyl, dec-9-enyl, dec-9-ynyl, decyl, undecyl, tridecyl, pentadecyl, 1-methylpentadecyl, 1,1-dimethylpentadecyl or heptadecyl, and acid addition salts thereof. When the group R contains a multiple bond between carbon atoms, the multiple bond may be located in any position of the hydrocarbon chain.

According to a feature of the present invention, the phenthiazine derivatives of formula I are prepared by the process which comprises reacting 3-dimethylsulphamoyl-10- 3-[4-(2-hydroxyethyl)-piperidino]-propyl phenthiazine of the formula:

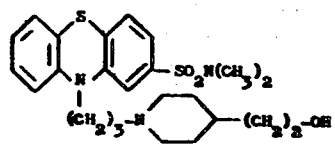

II with a compound of the general formula R—CO—X, wherein R is hereinbefore defined and X represents the acid residue of a reactive ester, for example a halogen atom, the hydroxy group, an alkoxy group containing from 1 to 4 carbon atoms, an imidazolyl group, or an alkanoyloxy, alkenoyloxy or alkynoyloxy group which may have a straight or branched hydrocarbon chain, and may, more particularly, be such that the compound R—CO—X represents the acid anhydride of formula R—CO—O—CO—R, R being as hereinbefore defined.

When the symbol X represents a halogen atom, in particular chlorine, or an imidazolyl, alkanoyloxy, alkenoyloxy or alkynoyloxy group, it is advantageous to carry out the process in an inert organic solvent (for example benzene, toluene or chloroform), and preferably at the boiling point of the solvent employed in the absence or presence of an inorganic or organic acid-binding agent.

When the symbol X represents the hydroxy group, the process is generally carried out in an inert organic solvent in the presence of either a strong acid or a Lewis acid or of dicyclohexylcarbodiimide.

When the symbol X represents an alkoxy group, the process is generally carried out in an inert organic solvent such as toluene and the alcohol formed is removed by azeotropic distillation.

According to a further feature of the invention, the phenthiazine derivatives of formula I are prepared by the process which comprises reacting a phenthiazine of the formula:

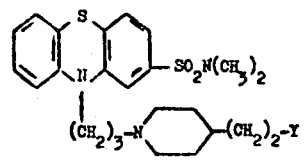

III wherein Y represents the acid residue of a reactive ester such as a halogen atom or a sulphuric ester residue (for example a methanesulphonyloxy or toluene-p-sulphonyloxy residue) with an alkali metal salt of an acid of the formula R—CO—OH (wherein R is as hereinbefore defined), the process being carried out in an inert organic solvent and preferably at the boiling point of the solvent employed.

The alcohol of formula II may be prepared, for example, by application of the processes described in the specification of our British Pat. No. 904208.

The phenthiazine compounds of general formula III may be prepared from the alcohol of formula II by applying any process which is known per se for replacing a hydroxy group by a reactive ester residue, such as Y defined above.

The phenthiazine derivatives of formula I obtained according to the foregoing processes may be purified by physical methods such as distillation, crystallisation or chromatography, or by chemical methods such as the formation of salts, crystallisation of the salts and decomposition of them in an alkaline medium. In the said chemical method, the nature of the anion of the salt is immaterial, the only requirement being that the salt must be well-defined and readily crystallisable. The phenthiazine derivative of formula I may be converted in manner known per se into acid addition salts. The acid addition salts may be obtained by the action of acids on the new phenthiazine derivatives in appropriate solvents. As organic there may be used, for example, alcohols, ethers, ketones or chlorinated hydrocarbons. The salt which is formed is precipitated, if necessary after concentration of its solution, and is separated by filtration or decantation.

The phenthiazine derivatives of the present invention have interesting pharmacodynamic properties; they are very active as long-acting neuroleptics, anti-emetics and tranquillisers. They have given good results as such in physiological experiments with animals at doses of 0.005 to 1.0 mg./kg. of animal weight by subcutaneous or intramuscular administration. For example, the compounds of formula I have been found to have a prolonged antagonistic effect against emesis caused by apomorphine in the dog. A subcutaneous dosage of one of the new compounds (as the free base) of 0.05 to 0.8 mg./kg. reduces the number of vomits caused by subcutaneous administration of 0.1 mg./kg. of apomorphine by 50% for from 10 to 50 days. The compounds of formula I have shown no toxic effects at dosages as least as high as 0.8 mg./kg. Preferred compounds are 3-dimethylsulphamoyl-10-{3-[4-(2-palmitoyloxyethyl)piperidino]propyl}-phenthiazine, 3-dimethylsulphamoyl-10-{3-[4-(2-undec-10'-enoyloxyethyl)-piperidino]propyl}phenthiazine, 3-dimethylsulphamoyl-10-{3-[4-(2-lauroyloxyethyl)piperidino]propyl} phenthiazine, 3-dimethylsulphamoyl-10-{3-[4-(2-2' methylhexadecanoyloxyethyl)piperidino] propyl}phenthiazine and 3-dimethylsulphamoyl-10-{3-[4-(2-2',2'-dimethylhexadecanoyloxyethyl)-piperidino]propyl}phenthiazine.

The following Examples illustrate the invention.

EXAMPLE I

3-Dimethylsulphamoyl-10-{3-[4-(2-hydroxyethyl)-piperidino]propyl}-phenthiazine (9.5 g.), palmitoyl chloride (5.5 g.) and anhydrous toluene (165 cc.) are heated under reflux for 5 hours. After cooling, the reaction mixture is stirred for 15 minutes in the presence of distilled water (200 cc.) and an aqueous 10% solution of sodium carbonate (50 cc.). The decanted organic solution is washed three times with distilled water (total 600 cc.) until neutral, dried over anhydrous magnesium sulphate and evaporated under reduced pressure (20 mm.Hg). The residue (14.9 g.), dissolved in acetone (50 cc.) under reflux, is treated with anhydrous oxalic acid (1.9 g.) dissolved in acetone (10 cc.). After 17 hours cooling at 3°C, the crystals which have appeared are filtered off, washed twice with ice-cooled acetone (total 50 cc.) and dried under reduced pressure (20mm.Hg). 3-Dimethylsulphamoyl-10-{3-[4-(2-palmitoyloxyethyl)piperidino]-propyl} phenthiazine oxalate (15.2 g.), melting at about 134°C, is obtained.

The palmitoyl chloride (b.p. 157°–166°C/0.2 mm.Hg) is prepared according to W. G. Rose, J. Am. Chem. Soc., 69, 1384 (1947).

3-Dimethylsulphamoyl-10-{3-[4-(2-hydroxyethyl)-piperidino]propyl}-phenthiazine employed as starting material is prepared by the procedure described in the specification of British Pat. No. 904208 by reacting 4-(2-hydroxyethyl)piperidine with 3-dimethylsulphamoyl-10-(3-hydroxypropyl)phenthiazine methanesulphonate.

EXAMPLE II

By following the procedure described in Example I but starting with 3-dimethylsulphamoyl-10-{3-[4-(hydroxyethyl)piperidino]-propyl}phenthiazine (9.5 g.), undec-10-enoyl chloride (4.05 g.) and toluene (165 cc.), 3-dimethylsulphamoyl-10-{3-[4-(2-undec-10'-enoyloxyethyl)piperidino-]propyl}phenthiazine oxalate (12.8 g.), melting at about 126°C, is obtained. -undec- Undec 10-enoyl chloride employed as starting material (b.p. 74°–75°C/0.2 mm.Hg) is prepared according to J. English et coll, J. Am. Chem. Soc., 67, 1413, (1945).

EXAMPLE III

By following the procedure described in Example I but starting with 3-dimethylsulphamoyl-10-{3-[4-(2-hydroxyethyl)piperidino]-propyl}phenthiazine (9.5 g.), lauroyl chloride (4.40 g.) and toluene (165 cc.), 3-dimethylsulphamoyl-10-{3-dimethylsulphamoyl-10-3-[4-(2-lauroyloxyethyl)piperidino]-propyl}phenthiazine oxalate (13.1g.), melting at about 130°C, is obtained.

Lauroyl chloride employed as starting material (b.p. 110°C/2 mm. Hg) is prepared according to H. Richet, Bull. Soc. Chim. Fr., (1946), 52.

EXAMPLE IV

By following the procedure 10- in Example I but starting with 3-dimethylsulphamoyl-10-{3-[4-(2-hydroxyethyl)piperidino]-propyl}phenthiazine (4.75 g.), decanoyl chloride (2.11 g.) and toluene (110 cc.), 3-dimethylsulphamoyl-10-{3-[4-(2-decanoyloxyethyl)-piperidino]propyl}phenthiazine oxalate (6.20g.), melting at about 134°C, is obtained.

Decanoyl chloride employed as starting material (b.p. 100°–102°C/10 mm.Hg) is prepared according to J. Casor et coll, J.Org. Chem. 26, 1768, (1961).

EXAMPLE V

By following the procedure described in Example I but starting with 3-dimethylsulphamoyl-10-{3-[4-(2-hydroxyethyl)piperidino]propyl}-phenthiazine (4.75 g.), 2-methylheptanoyl chloride (1.8 g.) and toluene (110 cc.), 3-dimethylsulphamoyl-10-{3-[4-(2-2'-methylheptanoyloxyethyl)piperidino]propyl}phenthiazine oxalate (6.1 g.), melting at about 156°C, is obtained.

2-Methylheptanoyl chloride employed as starting material (b.p. 60°–62°C/12 mm.Hg.) is prepared according to P. Xarrer et coll., Helv. Chim. Acta, 13, 1292, (1930).

EXAMPLE VI

By following the procedure described in Example I but starting with 3-dimethylsulphamoyl-10-{3-[4-(2-hydroxyethyl)piperidino]-propyl}phenthiazine (9.5 g.), 2,2-dimethylheptanoyl chloride (3.53 g.) and toluene (165 cc.), 3-dimethylsulphamoyl-10-{3-[4-(2-2',-2'-dimethylheptanoyloxyethyl) piperidino]propyl} phenthiazine oxalate (13.1 g.), melting at about 160°C, is obtained.

2,2-Dimethylheptanoyl chloride employed as starting material (b.p. 71.5°C/10 mm.Hg) is prepared according to M. Nuraya, Chem. Pharm. Bull. (Tokyo), 6, 186, (1958).

EXAMPLE VII

By following the procedure described in Example I but starting with 3-dimethylsulphamoyl-10-{3-[4-(2-hydroxyethyl)piperidino]propyl}phenthiazine (4.75 g.), 2-ethylhexanoyl chloride (1.8 g.) and toluene (100 cc.), 3-dimethylsulphamoyl-10-{3-[4-(2-2'-ethylhexanoyloxyethyl)piperidino]-propyl}phenthiazine oxalate (6.1 g.), melting at about 166°C, is obtained.

2-Ethylhexanoyl chloride employed as starting material (b.p. 71°–72°C/20 mm.Hg) is prepared according to E. H. Man et coll, J. Am. Chem. Soc., 73, 901 (1951).

EXAMPLE VIII

By following the procedure described in Example I but starting with 3-dimethylsulphamoyl-10-{3-[4-(2-hydroxyethyl)piperidino]propyl}-phenthiazine (4.75 g.), octanoyl chloride (1.76 g.) and toluene (110 cc.), 3-dimethylsulphamoyl-10-{3-[4-(2-octanoyloxyethyl)-piperidino]propyl}-phenthiazine oxalate (5.95 g.), melting at about 148°C, is obtained.

Octanoyl chloride employed as starting material (b.p. 96°–97°C/ 25 mm.Hg) is prepared according to J. Cason, J. Org. Chem., 23, 1492, (1958).

EXAMPLE IX

By following the procedure described in Example I but starting with 3-dimethylsulphamoyl-10-{3-[3-(2-hydroxyethyl)piperidino]propyl}-phenthiazine (4.75 g.) and undecanoyl chloride (2.3 g.) in toluene (100 cc.), 3-dimethylsulphamoyl-10-{3-[4-(2-undecanoyloxyethyl)piperidino]propyl}-phenthiazine oxalate (6.2 g.), melting at about 130°C, is obtained.

Undecanoyl chloride employed as starting material is prepared according to H. E. Fierz-David and W. Kuster, Helv. Chim. Acts., 22, 89 (1939).

EXAMPLE X

By following the procedure described in Example I but starting with 3-dimethylsulphamoyl-10-{3-[4-(2-hydroxyethyl)piperidino]propyl}-phenthiazine (4.7 g.) and nonanoyl chloride (1.95 g.) in toluene (100 cc.), 3-dimethylsulphamoyl-10-{3-[4-(2-nonanoyloxyethyl)piperidino]propyl}-phenthiazine oxalate (2.95 g.), melting at about 140°C., is obtained.

Nonanoyl chloride employed as starting material is prepared according to H. E. Fierz-David and W. Kuster, Helv. Chim. Acts, 22, 89 (1939).

EXAMPLE XI

By following the procedure described in Example I but starting with 3-dimethylsulphamoyl-10-{3-[4-(2-hydroxyethyl)piperidino]propyl}-phentiazine (4.75 g.) and undec-10-ynoyl chloride (2.2 g.) in toluene (100 cc.), 3-dimethysulphamoyl-10-{3-[4-(2-undec-10'-ynoyloxyethyl)-piperidino]propyl}phenthiazine oxalate (5 g.), melting at about 133°C., is obtained.

Undec-10-ynoyl chloride is prepared according to L. D. Bergel'son et coll, Zh. obshch, Khim., 32, 58 (1962); Chem Abstr., 57, 14930 b (1962).

EXAMPLE XII

By following the procedure described in Example I but starting with 3-dimethylsulphamoyl-10-{3-[4-(2-hydroxyethyl)piperidino]propyl}-phenthiazine (4.75 g.) and myristoyl chloride (3.7 g.) in toluene (100 cc.), 3-dimethylsulphamoyl-10-{3-[4-(2-myristoyloxyethyl)piperidino]propyl}-phenthiazine oxalate (6.3 g.), melting at about 134°C., is obtained.

Myristoyl chloride employed as starting material is prepared according to H. E. Fierz-David and W. Kuster, Helv. Chim. Acta., 22, 89 (1939).

EXAMPLE XIII

3-Dimethylsulphamoyl-10-{3-[4-(2-hydroxyethyl)-piperidino]-propyl}phenthiazine (4.75g.) is reacted with stearoyl chloride (3.34 g.) in toluene (100 cc.) according to the procedure described in Example I. After washing and evaporating the solvent, the resulting base is recrystallised from ethanol to give 3-dimethylsulphamoyl-10-{3-[4-(2-stearoyloxyethyl)-piperidino]propyl}phenthiazine (5.9 g.), melting at about 62°C.

Stearoyl chloride employed as starting material is prepared according to H. E. Fierz-David and W. Kuster, Helv. Chim. Acta, 22, 89 (1939).

EXAMPLE XIV

By following the procedure described in Example I but starting with 3-dimethylsulphamoyl-10-{3-[4-(2-hydroxyethyl)piperidino]propyl}-phenthiazine (9.5 g.) and dec-2-enoyl chloride (4.14 g.) in toluene (200 cc.), 3-dimethysulphamoyl-10-{3-[4-(2-dec-2'-enoyloxyethyl)piperidino]-propyl}phenthiazine oxalate (6.8 g.), melting at about 138°C., is obtained.

Dec-2-enoyl chloride employed as starting material prepared according to P. Van Romburgh, Rec. Trav. Chim. Pays-Bas 57, 494 (1938).

EXAMPLE XV

3-Dimethylsulphamoyl-10-{3-[4-(2-undec-10'-enoyloxyethyl)-piperidino]propyl}phenthiazine oxalate (308 g.), prepared as described in Example II, is suspended in distilled water (2 liters) and methylene chloride (1 liter). A 10% aqueous solution of sodium bicarbonate (1.250 liters) is added and the mixture is stirred for 5 minutes. After decantation of the organic phase, the aqueous phase is extracted twice with methylene chloride (total 1 liter). The organic phases are combined, washed three times with distilled water (total 1.5 liters) and dried over anhydrous sodium sulphate. After filtration, the solvent is removed by heating initially at 60°C. under ordinary pressure and then at 100°C. under reduced pressure (20 mm. Hg.). The crude oily base obtained (274 g.) is purified by chromatography through a column of neutral alumina (1 kg.) and elution with benzene (total 5.5 liters).

The benzene is then evaporated under reduced pressure (20 mm. Hg.) to yield the purified base (240 g.), which is dissolved at 60°C. in cyclohexane (650 cc.). After cooling to 40°C., petroleum ether (b.p. 40°–65°C., 1,350 cc.) is added. The mixture is cooled to 20°C., crystallisation of the product initiated, and then it is left for 2 hours at 20°C. and overnight at 3°C. The crystals which form are filtered off, washed twice with iced petroleum ether (300 cc. total) and dried under reduced pressure (20 mm. Hg.) to yield 3-dimethylsulphamoyl-10-{3-[4-(2-undec-10'-enoyloxyethyl)-piperidino]propyl}phenthiazine (222 g.) melting at 58°–59°C.

EXAMPLE XVI

3-Dimethylsulphamoyl-10-{3-[4-(2-hydroxyethyl)-piperidino]-propyl}phenthiazine (4.52 g.), 2-methylhexadecanoyl chloride (2.88 g.) and anhydrous toluene (50 cc.) are heated under reflux for 5 hours. After cooling, the reaction mixture is stirred for 1 hour in the presence of water (100 cc.) and an aqueous 10% solution of sodium carbonate (50 cc.). The decanted organic solution is washed three times with distilled water (total 100 cc.) until neutral, dried over anhydrous magnesium sulphate and evaporated under reduced pressure (20 mm. Hg.). The residue (6.9 g.) is dissolved in a mixture of cyclohexane and ethyl acetate (9–1 by volume); the solution is chromatographed through a column (1.7 cm. in diameter) containing neutral alumina (50 g.). After elution with a mixture (150 cc.) of cyclohexane and ethyl acetate (9–1 by volume), the eluates are evaporated under reduced pressure (15 mm. Hg.). The cystalline residue (6.1 g.) is recrystallised from petroleum ether (boiling point 40°–65°C.; 12 cc.). After 3 hours cooling at 5°C., the crystals are filtered off, washed twice with ice-cooled petroleum ether (5 cc.) and dried under reduced pressure (20 mm. Hg.) to yield 3-dimethylsulphamoyl-10-{3-[4-(2-2'-methylhexadecanoyloxy-ethyl)piperidino]propyl}-phenthiazine (4.6 g.) melting at about 55°C.

2-Methylhexadecanoyl chloride is prepared by the action of thionyl chloride on 2-methylhexadecanoic acid.

2-Methylhexadecanoic acid is prepared according to G. Weitzel et coll., Z. Physiol. Chem., 287, 65 (1951).

EXAMPLE XVII

Following the procedure described in Example XVI, 3-dimethylsulphamoyl-10-{3-[4-(2-hydroxyethyl)-piperidino]propyl}phenthiazine (3.3 g.) is reacted with 2,2-dimethylhexadecanoyl chloride (2.13 g.) in toluene (30 cc.). The crude product is chromatographed through a column (1.5 cm. in diameter) of neutral alumina (40 g.) and eluted with a mixture of cyclohexane and ethyl acetate (8–2 by volume). The base obtained after chromatography (4.70 g.) is dissolved in refluxing ethyl acetate (25 cc.) and then treated with anhydrous oxalic acid (0.57 g.) in solution in ethyl acetate (5 cc.). After 17 hours cooling at 3°C., the crystals which form are filtered off, washed twice with ice-cooled ethyl acetate (total 8 cc.) and dried under reduced pressure (20 mm. Hg.) to yield 3-dimethylsulphamoyl-10-{3-[4-(2-2',2'-dimethylhexadecanoyloxy-ethyl)piperidino]propyl}-phenthiazine oxalate (4.4 g.) melting at about 151°C.

2,2-Dimethylhexadecanoyl chloride is prepared by the action of thionyl chloride on 2,2-dimethylhexadecanoic acid.

2,2-Dimethylhexadecanoic acid is prepared according to Buu-Hoi et. coll., Z. Physiol. Chem. 279, 84 (1943).

The present invention includes within its scope pharmaceutical compositions containing, as active ingredient, at least one of the phenthiazine derivatives of formula I in association with a pharmaceutical carrier or coating. The invention includes especially such preparations made up for parenteral, in particular intramuscular or subcutaneous, administration.

Preparations for parenteral administration include sterile nonaqueous solutions. Examples of suitable non-aqueous solvents are injectable vegetable oils, such as sesame oil or olive oil, and injectable organic esters such as ethyl oleate. The preparations may be sterilised by, for example, filtration through a bacteria-retaining filter, by incorporation in the compositions of sterilising agents, by irradiation, or by heating.

The percentage of active ingredient in the compositions of the invention may be varied, it being necessary that it should constitute a proportion such that a suitable dosage shall be obtained. The dosage depends on the desired therapeutic effect and on the duration of the treatment. In human therapy the composition should generally be administered so as to give an adult between 5 mg. and 100 mg. of active substance at the rate of one intramuscular injection every two to four weeks.

Because of the prolonged anti-emetic effect of the new phenthiazine derivatives mentioned above, it is often desirable to administer the compounds by intramuscular or subcutaneous injection as depot preparations. Such preparations may be made by conventional methods, e.g. by dissolving the new bases of formula I in an injectable water-insoluble vegetable oil, e.g. in a concentration of 0.25 to 10% by weight, and, if necessary, subsequently sterilizing the solution obtained by filtration through a bacteriological filter.

The following Examples illustrate the preparation of pharmaceutical compositions according to the invention.

EXAMPLE XVIII

3-Dimethylsulphamoyl-10-{3-[4-(2-lauroyloxyethyl)piperidino]-propyl}phenthiazine oxalate (170 mg.) is treated at ambient temperature with a mixture of a 1% aqueous solution of sodium bicarbonate (110 cc.) and diethyl ether (50 cc.). After dissolution, the ethereal phase is decanted, washed with distilled water (2 × 50 cc.) until neutral, and then dried over anhydrous magnesium sulphate. After concentration under reduced pressure (20 mm. Hg.), the residue (150 mg.) is dissolved in sesame oil (15 cc.) at 40°C. After cooling to ambient temperature, a clear yellow solution containing 1% of 3-dimethylsulphamoyl-10-{3-[4-(2-lauroyloxyethyl)piperidino]propyl}phenthiazine is obtained.

EXAMPLE XIX

3-Dimethylsulphamoyl-10-{3-[4-(2-undec-10'-enoyloxyethyl)piperidino]propyl}phenthiazine (2.5 g.) is dissolved at 40°C. in neutralised sesame oil (100 cc.) with agitation. After cooling, the yellow solution obtained is filtered through a bacteriological filter under a nitrogen pressure of 2 kg./cm². The filtered solution is then aseptically distributed into 5 cc. ampoules giving 4.1 cc. of solution per ampoule. The filled ampoules are sealed under nitrogen.

The resulting ampoules each contain 100 mg. of active product ready for intramuscular administration.

EXAMPLE XX

By proceeding as described in Example XIX but using 3-dimethylsulphamoyl-10-{3-[4-(2-palmitoyloxyethyl)piperidino]propyl}phenthiazone, m.p. 61°–62°C., ampoules are obtained each containing 100 mg. of active product.

We claim:
1. The phenthiazine derivative which is 3-Dimethyl-sulphamoyl-10-{3-[4-(2-2'-methylhexadecanoyloxy-ethyl)piperidino]propyl}phenthiazine.
2. The phenthiazine derivative which is 3-Dimethyl-sulphamoyl-10-{3-[4-(2-2',2'-dimethylhexadecanoyloxyethyl)piperidino]propyl}phenthiazine.

\* \* \* \* \*

UNITED STATES PATENT OFFICE
CERTIFICATE OF CORRECTION

Patent No. 3,959,268                        Dated  May 25, 1976

Inventor(s) Jean-Claude Rene Georges Blondel et al.

It is certified that error appears in the above-identified patent and that said Letters Patent are hereby corrected as shown below:

Under "Foreign Application Priority Data", the number of the French Priority Application should be changed from "67.1000663" to correctly read --67.100663--.

Signed and Sealed this

Twelfth Day of April 1977

[SEAL]

*Attest:*

RUTH C. MASON
*Attesting Officer*

C. MARSHALL DANN
*Commissioner of Patents and Trademarks*